US009844137B2

(12) United States Patent
Fathauer

(10) Patent No.: US 9,844,137 B2
(45) **Date of Patent: *Dec. 12, 2017**

(54) PRINTED CIRCUIT ASSEMBLY FOR A SOLENOID MODULE FOR AN AUTOMATIC TRANSMISSION

(71) Applicant: Advanced Powertrain Engineering, LLC, Sullivan, IN (US)

(72) Inventor: Paul Fathauer, Sullivan, IN (US)

(73) Assignee: Advanced Powertrain Engineering, LLC, Sullivan, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/850,253

(22) Filed: Sep. 10, 2015

(65) Prior Publication Data

US 2016/0198573 A1 Jul. 7, 2016

Related U.S. Application Data

(63) Continuation of application No. 13/119,041, filed as application No. PCT/US2009/057514 on Sep. 18, 2009, now Pat. No. 9,198,301.

(Continued)

(51) Int. Cl.
*H05K 1/11* (2006.01)
*H05K 3/34* (2006.01)

(Continued)

(52) U.S. Cl.
CPC .............. *H05K 1/115* (2013.01); *F16K 31/02* (2013.01); *H05K 1/119* (2013.01); *H05K 1/18* (2013.01);

(Continued)

(58) Field of Classification Search
CPC ........ H05K 1/115; H05K 1/116; H05K 1/119; H05K 3/3447; H05K 3/42;

(Continued)

(56) References Cited

U.S. PATENT DOCUMENTS 3,477,055 A 11/1969 Herbst
4,160,503 A 7/1979 Ohlbach (Continued)

FOREIGN PATENT DOCUMENTS

EP 0797008 5/2001
EP 1574770 12/2006

(Continued)

OTHER PUBLICATIONS

Doman, C.T. and R.I. Rice, Jr., "Parts Salvage—When Does it Pay to rebuild Parts?", SAE Sep. 30, 1961.

(Continued)

*Primary Examiner* — Hoa C Nguyen
*Assistant Examiner* — Christopher L Augustin
(74) *Attorney, Agent, or Firm* — John V. Daniluck; Bingham Greenebaum Doll LLP

(57) ABSTRACT

A printed circuit assembly (PCA) that provides for a method of rebuilding an electrically operated automatic transmission solenoid module. The PCA allows for a repairable yet rugged interconnection of several solenoids that reside within the span of the module assembly.

20 Claims, 16 Drawing Sheets

Related U.S. Application Data

(60) Provisional application No. 61/098,117, filed on Sep. 18, 2008.

(51) Int. Cl.
*H05K 3/42* (2006.01)
*F16K 31/02* (2006.01)
*H05K 1/18* (2006.01)

(52) U.S. Cl.
CPC ............. *H05K 3/3447* (2013.01); *H05K 3/42* (2013.01); *H05K 2201/09854* (2013.01); *H05K 2201/1003* (2013.01); *H05K 2201/10303* (2013.01); *H05K 2201/10818* (2013.01); *Y10T 29/49002* (2015.01)

(58) Field of Classification Search
CPC . H05K 2201/1003; H05K 2201/09854; H05K 2201/10303; H05K 2201/10818
See application file for complete search history.

(56) References Cited

U.S. PATENT DOCUMENTS 4,429,459 A 2/1984 Lynch
4,678,006 A 7/1987 Northman et al.
4,783,049 A 11/1988 Northman et al.
4,785,848 A 11/1988 Lieber
4,787,853 A 11/1988 Igarashi
4,932,439 A 6/1990 McAuliffe, Jr.
4,947,893 A 8/1990 Miller et al.
4,959,750 A 9/1990 Cnyrim et al.
4,980,217 A * 12/1990 Grundfest ............ B29C 70/202 174/255
5,090,109 A 2/1992 Haas et al.
5,093,183 A 3/1992 Strunka
5,121,769 A 6/1992 McCabe et al.
5,127,440 A 7/1992 Maas et al.
5,129,145 A 7/1992 Matthews et al.
5,135,027 A 8/1992 Miki et al.
5,184,644 A 2/1993 Wade
5,217,047 A 6/1993 McCabe
5,449,227 A 9/1995 Steinberg et al.
5,452,948 A 9/1995 Cooper et al.
5,611,372 A 3/1997 Bauer et al.
5,651,391 A 7/1997 Connolly et al.
5,680,883 A 10/1997 Gluf
5,823,070 A 10/1998 Taniguchi et al.
5,823,071 A 10/1998 Petrosky et al.
5,855,229 A 1/1999 Gluf, Jr.
5,887,851 A 3/1999 Trzmiel
5,904,180 A 5/1999 Iwamura et al.
6,019,120 A 2/2000 Najmolhoda et al.
6,038,918 A 3/2000 Newton
6,045,025 A 4/2000 Muramatsu et al.
6,056,908 A 5/2000 Petrosky et al.
6,057,027 A 5/2000 Roy
6,109,300 A 8/2000 Najmolhoda
6,155,137 A 12/2000 Nassar et al.
6,161,577 A 12/2000 Nassar
6,164,160 A 12/2000 Nassar et al.
6,164,732 A 12/2000 Tominaga et al.
6,269,827 B1 8/2001 Potter
6,354,674 B1 3/2002 Iwamoto et al.
6,450,424 B1 9/2002 Horbelt
6,530,856 B1 3/2003 Kakiage
6,544,138 B2 4/2003 True et al.
6,612,202 B2 9/2003 Thorum et al.
6,713,685 B1 3/2004 Cotton
6,715,510 B2 4/2004 Hebert
6,761,596 B2 7/2004 Kuhbauch et al.
6,832,632 B1 12/2004 Wallace
6,894,217 B2 5/2005 Li
7,051,993 B2 5/2006 Kim et al.
7,055,549 B2 6/2006 Flynn et al.
7,086,308 B2 8/2006 Suzuki et al.
7,104,273 B1 9/2006 Stafford
7,110,246 B2 9/2006 Tsunooka et al.
7,220,085 B2 5/2007 Nader et al.
7,233,503 B2 6/2007 Chen
7,572,402 B2 8/2009 Roskowski et al.
7,707,872 B2 * 5/2010 Herbert ............... F15B 13/0814 73/49.7
7,771,144 B1 8/2010 Nader et al.
7,983,024 B2 7/2011 Harris
8,387,254 B2 3/2013 Fathauer
9,198,301 B2 11/2015 Fathauer
2002/0185307 A1 12/2002 Gurel et al.
2003/0136656 A1 * 7/2003 Dunne ................ H01H 1/5805 200/292
2007/0089903 A1 * 4/2007 Huang ................... H05K 1/116 174/262
2008/0089044 A1 4/2008 Fathauer
2009/0017647 A1 * 1/2009 Horiuchi .............. H05K 1/0263 439/76.1
2009/0124099 A1 5/2009 Chen
2009/0217523 A1 9/2009 Johnson et al.
2013/0333218 A1 12/2013 Fathauer

FOREIGN PATENT DOCUMENTS

WO 2008040944 4/2008
WO 2010033827 3/2010

OTHER PUBLICATIONS

"How to Repair Solenoids for Ford PMGR, Delco PMGR and Delco SD210/260 Starters," Technical Update 25, 87-254-1 Jan. 31, 1995.
"AW Solenoid Tool Part #31333", Omega Machine & Tool, Inc. Dec. 31, 2020.
"Sonnax Transmission Products Catalog", 2010, Sonnax Industries, vol. 8, pp. 63, 146, 158 Dec. 31, 2010.
Stafford, Maura, "Restoring the Valve Bore: Reamer Technique", Sonnax Industries, pp. 164-167 Dec. 31, 2021.
Gran et. al., "Impact of Microvia-IN-Pad Design on Void Formation," www.sanmina.com (Sanmina Corp.), Jun. 2000. Jun. 1, 2000.
Serial No. PCT/US2009/057514, Search Report & Written Opinion, dated Nov. 18, 2009.
Serial No. PCT/US2009/057514, Response to Written Opinion, dated Jul. 19, 2010.
Serial No. PCT/US2009/055714, International Preliminary Report on Patentability, dated Aug. 10, 2012.
U.S. Appl. No. 13/119,041, Office Action, dated Dec. 11, 2013.
U.S. Appl. No. 13/119,041, Office Action, dated Sep. 4, 2014.
Submission to Satisfy Duty of Disclosure for Design U.S. Appl. No. 29/540,243, dated Apr. 8, 2016.
U.S. Appl. No. 13/119,041, Notice of Allowance dated May 18, 2015.
U.S. Appl. No. 13/119,041, Response to Office Action dated Apr. 11, 2014.
U.S. Appl. No. 13/119,041, Response to Office Action dated Jan. 5, 2015.

* cited by examiner

PRINTED CIRCUIT ASSEMBLY FOR A SOLENOID MODULE FOR AN AUTOMATIC TRANSMISSION

This application is a continuation of U.S. application Ser. No. 13/119,041, filed Mar. 15, 2011, which is the National Stage of International Application No. PCT/US2009/057514, filed Sep. 18, 2009, which claims the benefit of U.S. Provisional Application No. 61/098,117, filed Sep. 18, 2008, the entireties of which are hereby incorporated herein by reference. Any disclaimer that may have occurred during the prosecution of the above-referenced applications is hereby expressly rescinded.

FIELD OF THE INVENTION

The present invention pertains to methods for attaching a hydromechanical valve to a circuit assembly, and in particular to rebuilding a printed circuit assembly of an electrohydraulic assembly.

BACKGROUND OF THE INVENTION

Within the field of the automotive aftermarket, there are numerous parts that are considered to be "non-serviceable" items. In such cases, a new part is purchased at a substantial cost to the end user. In the field of automatic transmissions, one such common device is the solenoid module assembly that controls hydraulic flow and pressure within the transmission. A typical solenoid module includes a hydraulic manifold and one or more electromechanical solenoids. The hydraulic manifold contains numerous fluid circuit passages that hydraulically communicate with the solenoids. The electromechanical solenoids control either the flow (on/off control) through the passages or regulate pressure within the passages. Typically, the solenoids are electrically connected to a terminal housing that provides for a removable connection to a wire harness, allowing for communication to the powertrain control unit (PCU).

One such apparatus is described in U.S. Pat. Nos. 4,678,006 and 4,783,049. In the disclosure, a device including five electrically actuated solenoid assemblies are situated on an aluminum manifold block including multiple fluid passageways. The connections for the solenoids includes round pins that extrude upwards through a circuit board and are soldered into place. The circuit board consists of strips of copper forming circuit tracks that are further encased in plastic, herein generally referred to as a circuit board assembly (CBA). The CBA interconnects to a terminal connector providing communication through a wire harness to the PCU. This particular solenoid module is used in the Ford E4OD and 4R100 automatic transmission since 1989. It has several well-known failure modes and is a common replacement item. These new modules typically cost $150-200 to the end user.

Another such apparatus is described in U.S. Pat. No. 6,056,908. The disclosure is for a method of producing a solenoid module assembly with similar features to the '006 and '049 patents. In this design, an overmolded circuit assembly is described where circuit tracks are formed from strips of beryllium copper and overmolded with plastic. Furthermore, connection with the solenoids and terminal connection is preferably through the use of M shaped slots in which the solenoid terminals are pressed through, creating a friction type connection. The connection between the solenoid terminal and circuit track is made by the pressure generated from the displaced slot. This forms a one-way barbed type connection that prevents easy removal of the circuit track. This may prevent the slot from "backing off" the solenoid terminal. However, this connection style inhibits the removal of the circuit assembly for servicing. One feature of this style of connection is that rectangular pins are used.

A variation of the '908 design is the solenoid module 50P produced by Bosch that is used in the 2002-2003 Ford 5R55W, 2004-up 5R55S and the 1999-up 5R55N automatic transmissions. This module is shown in FIG. 1. This solenoid module has high failure rates, similar to the E4OD/4R100 solenoid module described in the '006 and '049 patents. This solenoid module costs the end user between $200-300. There has been extensive interest in rebuilding this module as generally the failure is localized to an individual solenoid (56P) (57P) (58P) or a broken circuit track (71P) within the assembly. However, the major obstacle has been the CBA that cannot be easily removed in one piece for reuse.

The CBA 70P includes multiple circuit tracks 71P that are placed within two plastic housings 72P and 74P that are snapped together, sandwiching the circuit tracks into place. During the removal process, the circuit assembly 71P flexes, which releases the snapped connections between the two housings 72P and 74P, and results in the circuit tracks to fall out of location.

FIG. 2 is a picture of the 5R55 module from the CBA side. FIG. 3 is a picture of a CBA without the top housing half, exposing the internal circuit tracks 71P. FIG. 4 is an enlarged picture of the terminal connection area, which shows spring-loaded frictional fits in the form of the barbed, press-fit connections 78P. In this figure, the rectangular configuration of the pins 77P can be seen clearly. FIG. 5 is a picture of typical results when attempting removal of the CBA. In this figure, it can be seen that the circuit tracks have snapped out of position, and the barbed connection 78P are no longer in reliable electrical communication with the internal circuitry of circuit tracks 71P. FIG. 6 is a picture of the module 50P after removal of the CBA 70P and manifold 52P. FIG. 7 is a picture of a failed circuit track within the assembly.

What is needed is a reliable, low cost method to rebuild electro-hydromechanical assemblies. Various embodiments of the present invention do this in novel and nonobvious ways.

SUMMARY OF THE INVENTION

Some embodiments of the present invention relates to a fluid control device including several actuators, such as but not limited to solenoids, arranged and secured within a manifold block. This solenoid block assembly or module is primarily adapted for automatic transmissions used in motor vehicles; however, the present invention is not so limited, and can be used in any application involving the interconnection of the electrical leads of any kind of actuator to a printed circuit assembly.

Yet other embodiments pertain to a printed circuit assembly (PCA) that allows for rebuilding a solenoid module. In some embodiments a new PCA replaces an original, non-soldered circuit assembly, providing for quicker replacement and improved connection. In yet other embodiments, a printed circuit assembly (including etched circuit paths or circuit traces) replaces an existing circuit board assembly, such as a CBA including strips of conductive material placed within nonconductive material such as plastic.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is excessive and unnecessary.

DESCRIPTION OF THE PREFERRED EMBODIMENT

Figure 1:
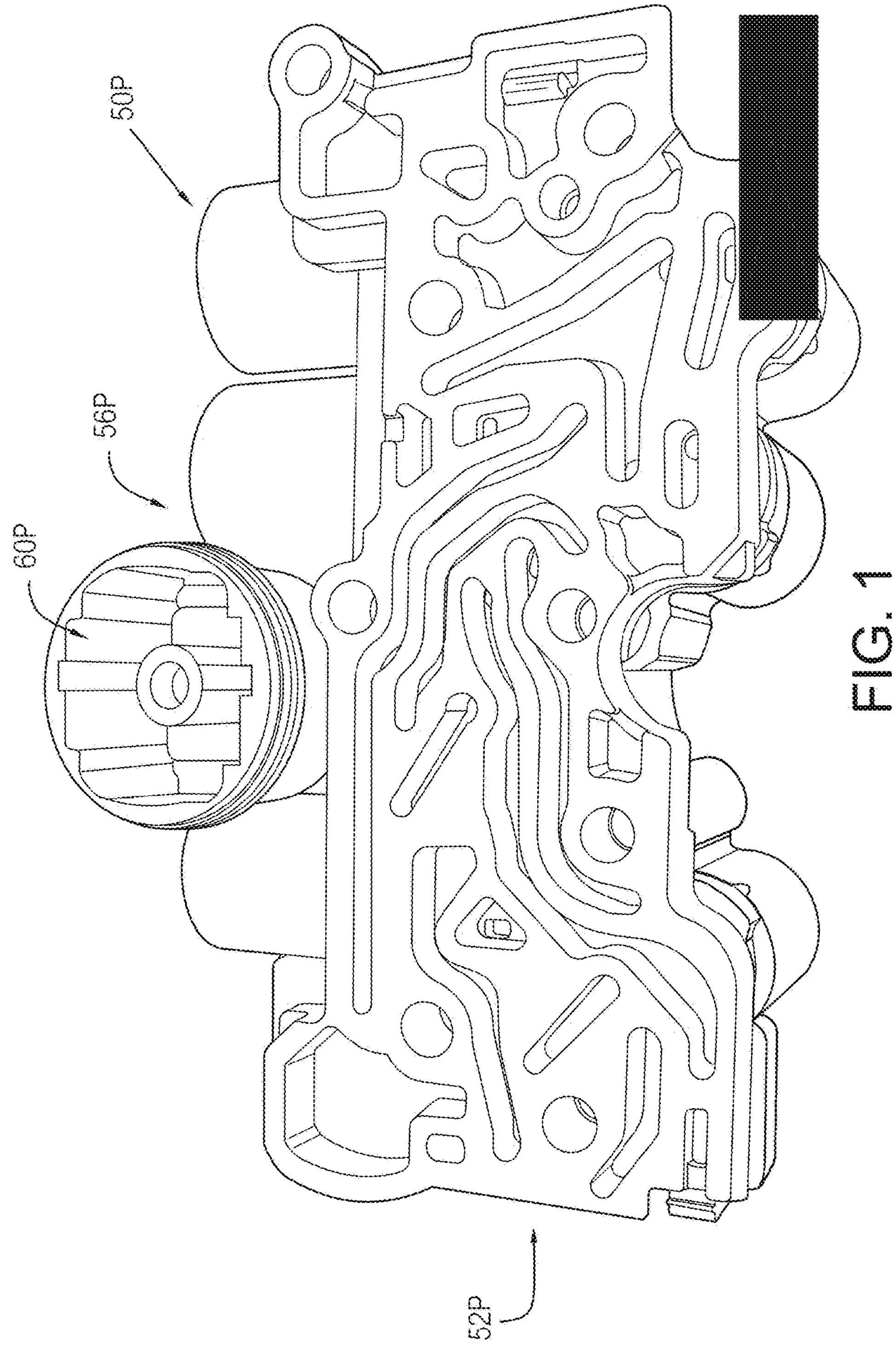
FIG. 1: An existing solenoid module
Figure 2:
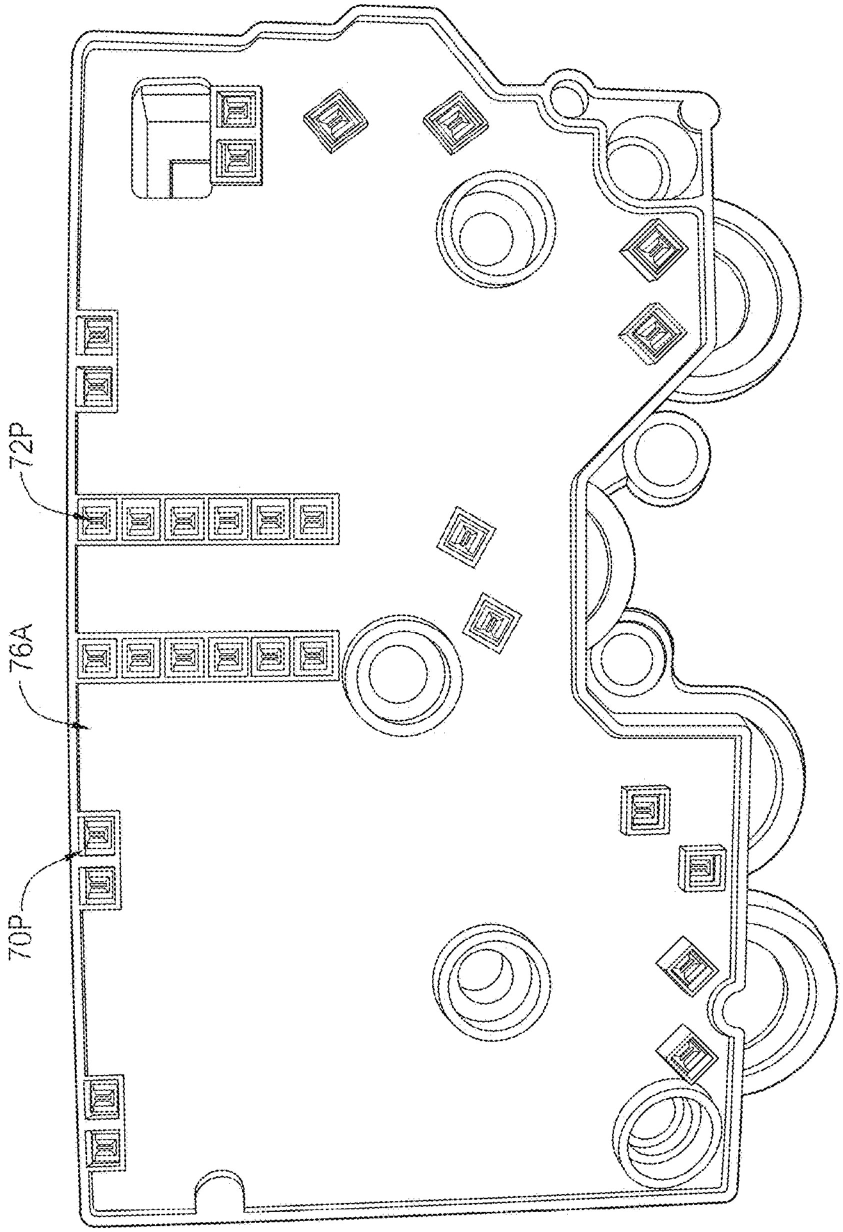
FIG. 2: The solenoid module of FIG. 1 from circuit assembly side, with interconnections intact.
Figure 3:
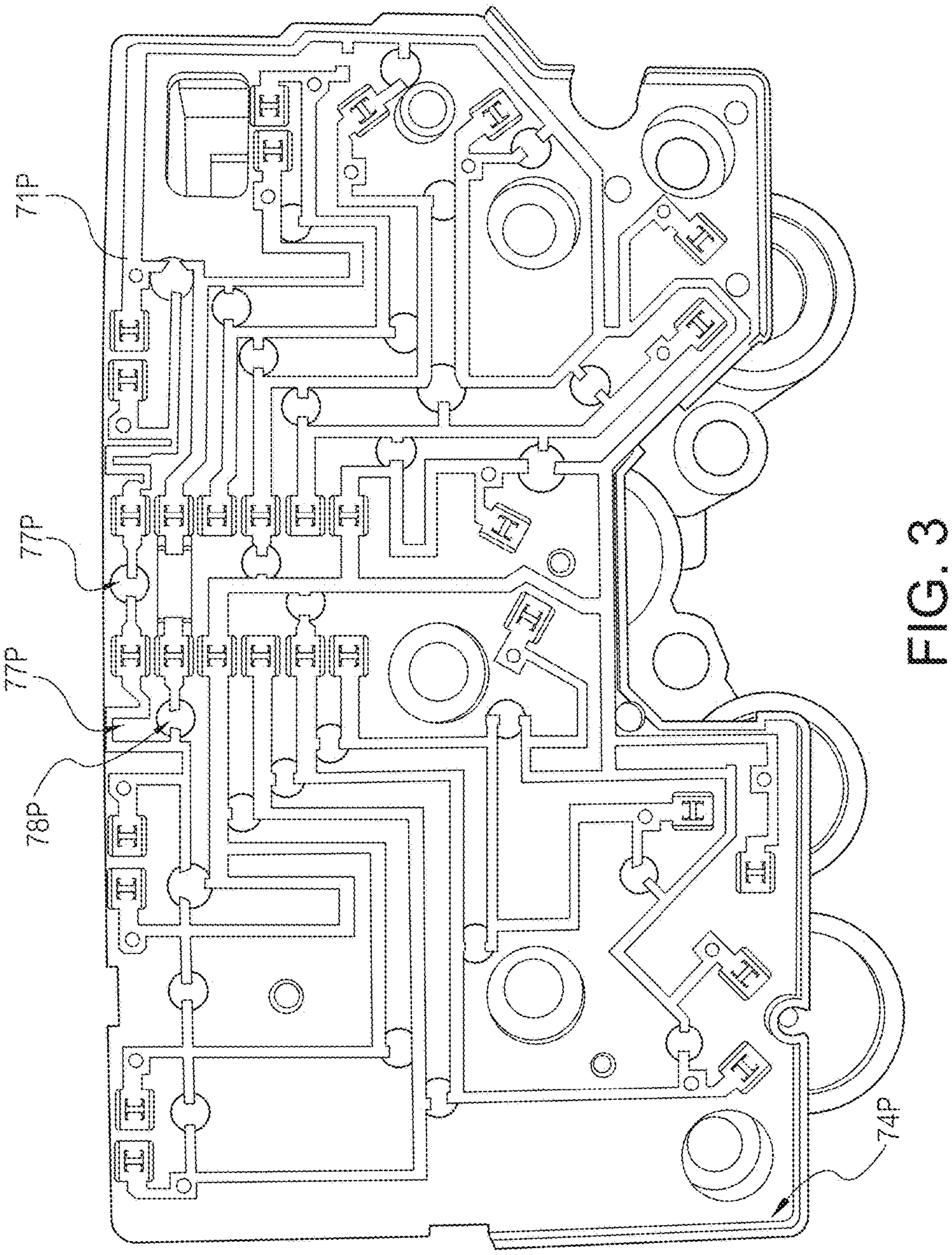
FIG. 3: The solenoid module from circuit assembly side without top assembly housing
Figure 4:
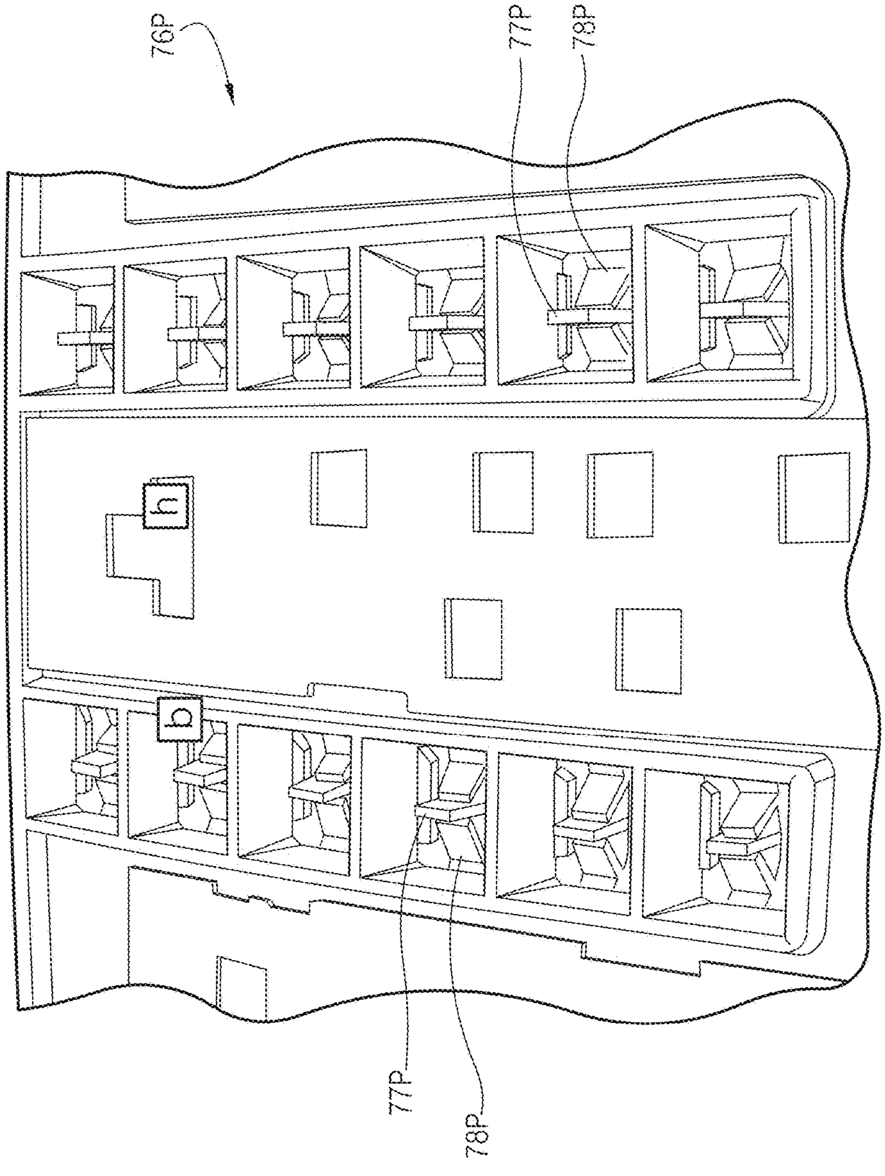
FIG. 4: Circuit assembly barbed connection from FIG. 2.
Figure 5:
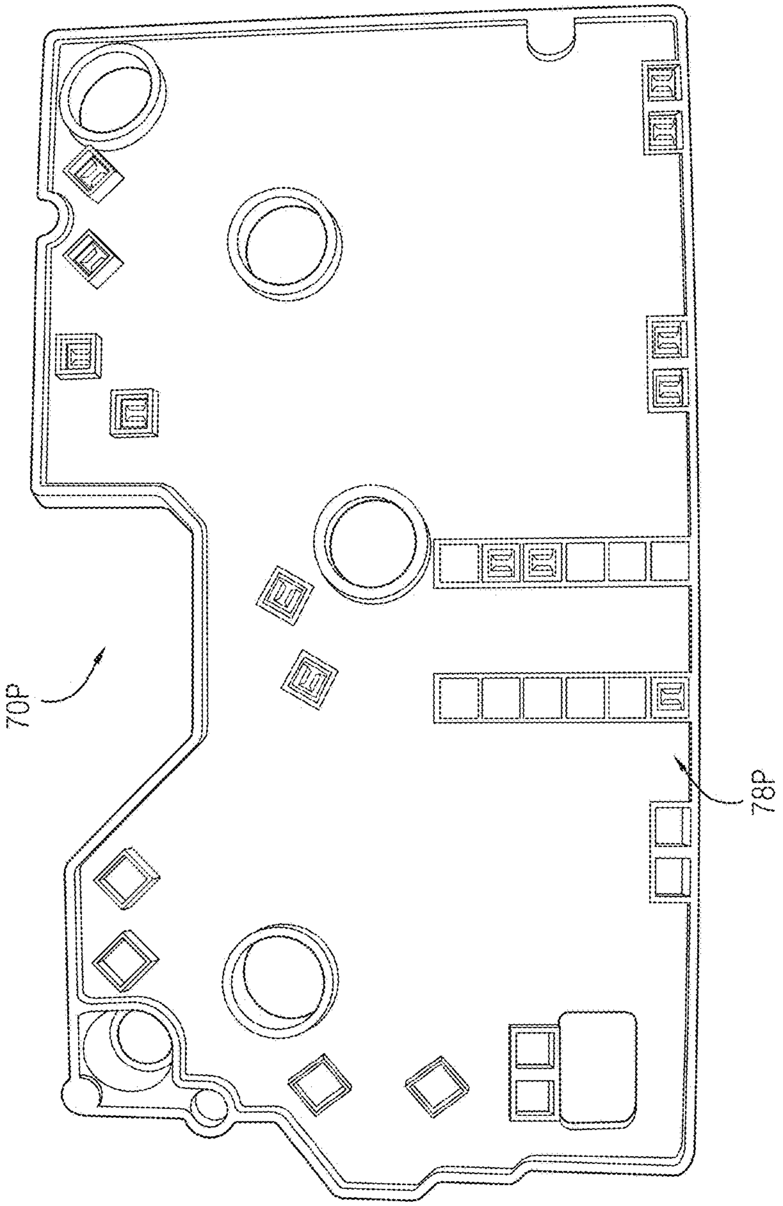
FIG. 5: Typical results after circuit assembly removal for apparatus of FIG. 2, with the interconnections broken.
Figure 6:
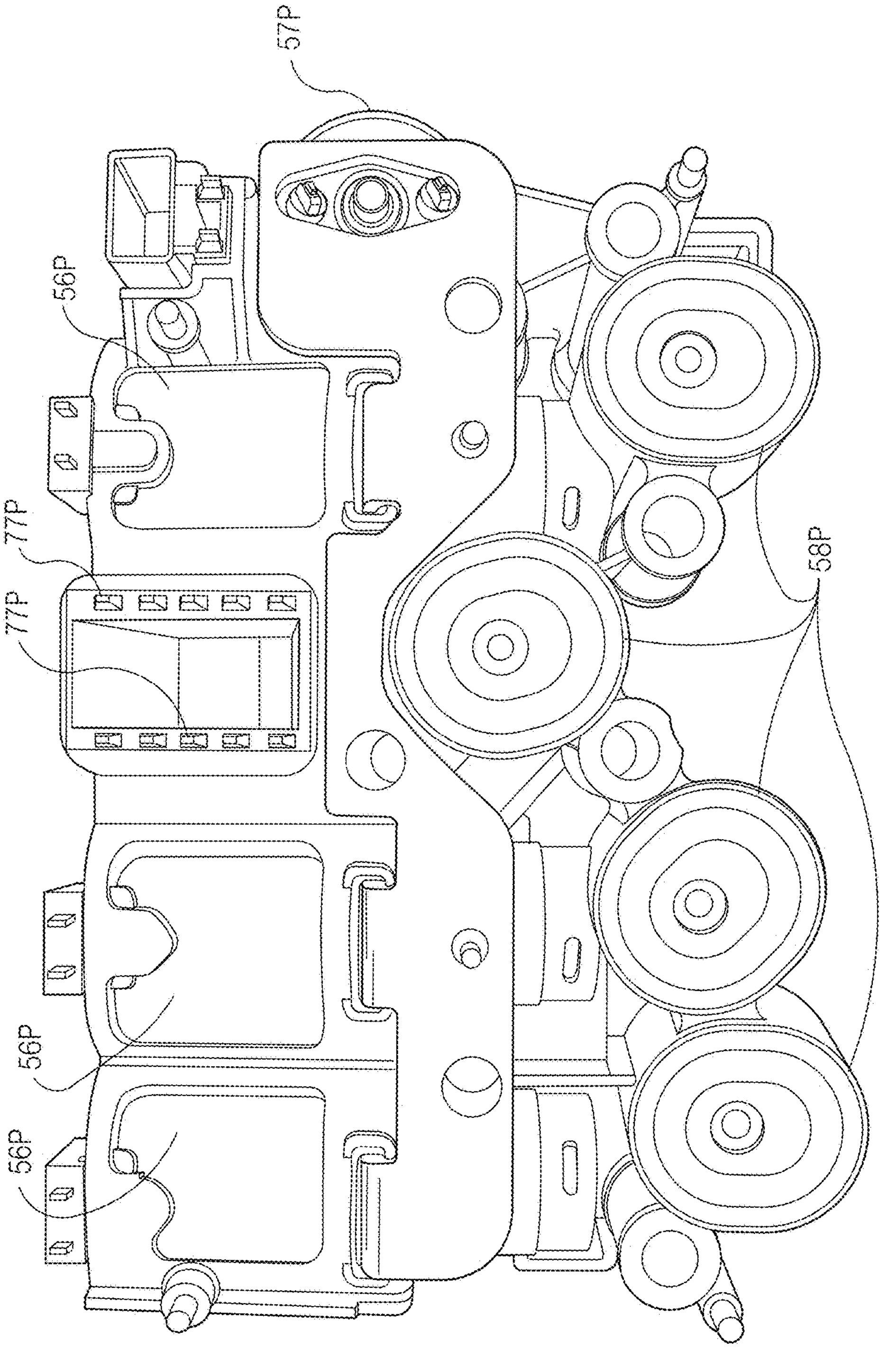
FIG. 6: Solenoid module of FIG. 1 from circuit assembly side after circuit assembly removal

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention. It is understood that any reference to "the invention" is a reference to an embodiment of a family of inventions, with no single embodiment including an apparatus, process, or composition that must be included in all embodiments, unless otherwise stated.

The use of an N-series prefix for an element number (NXX.XX) refers to an element that is the same as the non-prefixed element (XX.XX), except as shown and described thereafter. As an example, an element 1020.1 would be the same as element 20.1, except for those different features of element 1020.1 shown and described. Further, common elements and common features of related elements are drawn in the same manner in different figures, and/or use the same symbology in different figures. As such, it is not necessary to describe the features of 1020.1 and 20.1 that are the same, since these common features are apparent to a person of ordinary skill in the related field of technology. Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples only. Further, with discussion pertaining to a specific composition of matter, that description is by example only, and does not limit the applicability of other species of that composition, nor does it limit the applicability of other compositions unrelated to the cited composition.

Those element numbers that are followed with "P" refer to elements pertaining to known designs.

One embodiment of the present invention is a printed circuit assembly (PCA) with an interconnect opening that allows for the rectangular style terminal pins to connect to the assembly instead of a CBA. Whereas A PCA includes a printed circuit board (PCB) including etched, conductive circuit paths, as well as other installed components such as electronic components including thermistors, diodes, resistors, etc.

Many existing solenoid assemblies of automatic transmissions use a circuit board assembly (CBA) to interface electrical signals from a computer controller to the electro-hydraulic valves that turn the electrical signals into fluid power within the automatic transmission. Since the transmission fluid is hot (in excess of 300 F) and the transmission's internal environment is mechanically challenging (from gear train vibration and engine vibration), the solenoid assembly needs to be rugged.

A CBA includes individual strips of conductive material, such as copper, forming circuit paths and encased in plastic, for example either overmolded plastic or a plastic sandwich. Further, many CBAs include electrical connections to solenoids or other components that are chosen for the ability of the connector to withstand the harsh environment, but often these connections are intended to be made permanently and quickly in a high production environment. These CBA assemblies and connectors have been chosen for various reasons, including their ruggedness in the extreme vibration, temperature, and contamination environment within the inside of an automatic transmission, but the connectors in particular are seriously compromised with respect to reparability. However, reparability often becomes an issue because other components within the solenoid assembly are not as rugged as the CBA, and these other components may fail prematurely. When these failures take place, even when the failures are simple and readily identifiable, the entire solenoid assembly is often discarded because the electrical connections of the CBA are irreparably damaged during disassembly. Discarding these solenoid assemblies is an economic problem and an environmental problem.

One embodiment of the present invention is shown in FIGS. 8 to 19. Solenoid Assembly 50 includes a printed circuit assembly 20 with connection features that are sufficiently rugged to withstand the transmission internal environment, yet still be repairable. FIGS. 8*a* and 8*b* show interconnect opening of PCA 20 according to two embodiments. The interconnect openings 23 of the PCA 20 can be soldered onto the terminal pins 77 of the existing solenoids 56, which is a more secure connection and allows for ease of future servicing of the module. In addition, the embodiment is an improvement over existing designs by reducing the occurrence of broken circuit tracks, such as that shown in FIG. 7. This embodiment enables the rebuilding of such solenoid modules, including repair or replacement of individual elements within the module, providing an alternative to the expensive new modules. It is estimated that a rebuilt module would cost about 50% of a new one.

Figure 8A:
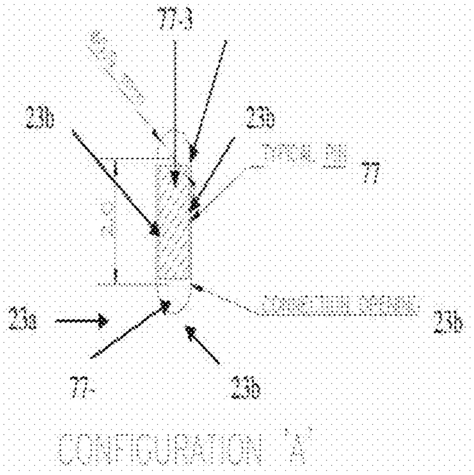
FIG. 8*a*: Connection hole configuration according to one embodiment of the present invention.
Figure 8B:
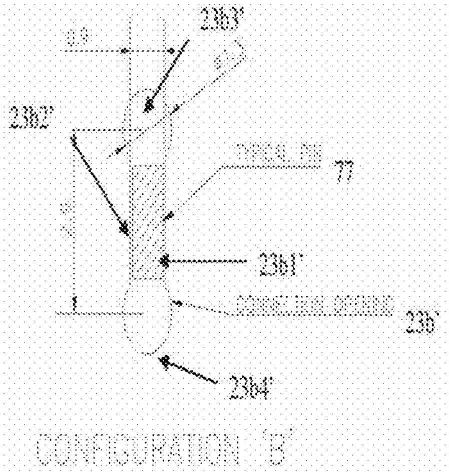
FIG. 8*b*: Connection hole configuration according to another embodiment of the present invention.

An apparatus according to one embodiment of the present invention comprises a PCA that has connection openings according to FIGS. 8*a* and 8*b*. FIG. 8*a* shows a pin 77 inserted within a hole 23*b* of a printed circuit assembly 21. An interconnect area 23*a* comprising a conductive material surrounds opening 23*b*. Opening 23*b* includes generally parallel sides 23*b*1 and 23*b*2 interconnected at top and bottom (with reference to orientation of FIG. 8*a*) by rounded edges 23*b*3 and 23*b*4. Preferably, the rounded ends 23*b*3 and 23*b*4 of opening 23*b* are semi-circular, although the present invention further contemplates those designs in which the ends are not rounded, but are any curved design that preferably avoids sharp corners. As another example, some embodiments of the present invention contemplate the use of a substantially rectangular opening in the PCA that includes rounded corners.

Preferably, the opposing ends of connection opening 23*b* are sufficiently large so as to provide clearance from respective end edges 77-3 and 77-4 of pin 77. Typical clearance is about 0.05 mm/side along the parallel sides. Rounded ends of the connection opening 23*b* are preferred in some embodiments in order to reduce corner stresses in the circuit card itself.

FIG. 8*b* shows an alternative embodiment. A connection opening 23*b*' is defined within a printed circuit assembly 21' for interconnection with a generally rectangular cross sectioned pin 77. Opening 23*b*' includes first and second parallel sides that are interconnected at either end with rounded ends 23*b*3' and 23*b*4'. These rounded ends are generally circular in area. However, the diameter of the defined circular end is greater than the width between the parallel sides 23*b*1' and 23*b*2'. By introducing a larger diameter at the ends, a further reduction in the concentration of flexing stresses within the printed circuit assembly can be expected.

Figure 8C:
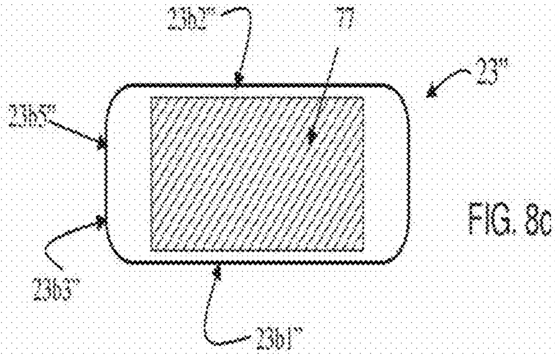
FIG. 8*c*: Connection hole configuration according to another embodiment of the present invention.

FIG. 8*c* shows another alternative embodiment. A connection opening 23*b*" is defined within a printed circuit assembly 21" for interconnection with a generally rectangular cross sectioned pin 77. Opening 23*b*" includes first and second parallel sides that are interconnected at either end with rounded corners 23*b*3", each pair of rounded corners being interconnected with a straight section 23*b*5". These rounded corners are generally circular. By introducing a larger diameter corners at the ends of a substantially rectangular hole 23", a further reduction in the concentration of flexing stresses within the printed circuit assembly can be expected.

The preferred dimensions (in millimeters) are shown in FIG. 8 only for illustrative purposes. The PCA connection openings allow for insertion onto a rectangular pin and soldered connections along the lengths. Preferably, the clearance provided at the ends of the slot (between the ends of the pin and the facing edges of the connection opening) are not so great that a solder connection is not made.

In one embodiment, the printed circuit board (PCB) of described PCA is comprised of the Flame Retardant 4 (FR-4) epoxy resin material for the core. The board is plated with copper on one side to create the interconnection traces (22) between the solenoids and terminal connector 60 and the front side connection pads (23*a*). A further copper layer is deposited creating the back side connection pads (23*c*) and the thru hole wall (23*b*). This provides a conductive material on the through, interconnection holes for mating with the pins. A green solder mask is applied over both sides of the assembly, except in the areas of the connection openings (23*a*)(23*c*) and walls (23*b*). In the areas around the connection openings (23*a*)(23*c*) and walls (23*b*), a solder coating is applied over the copper. This coating assists the soldering process when installing the assembly on the module and protects the copper in these areas from oxidization.

Figure 9:
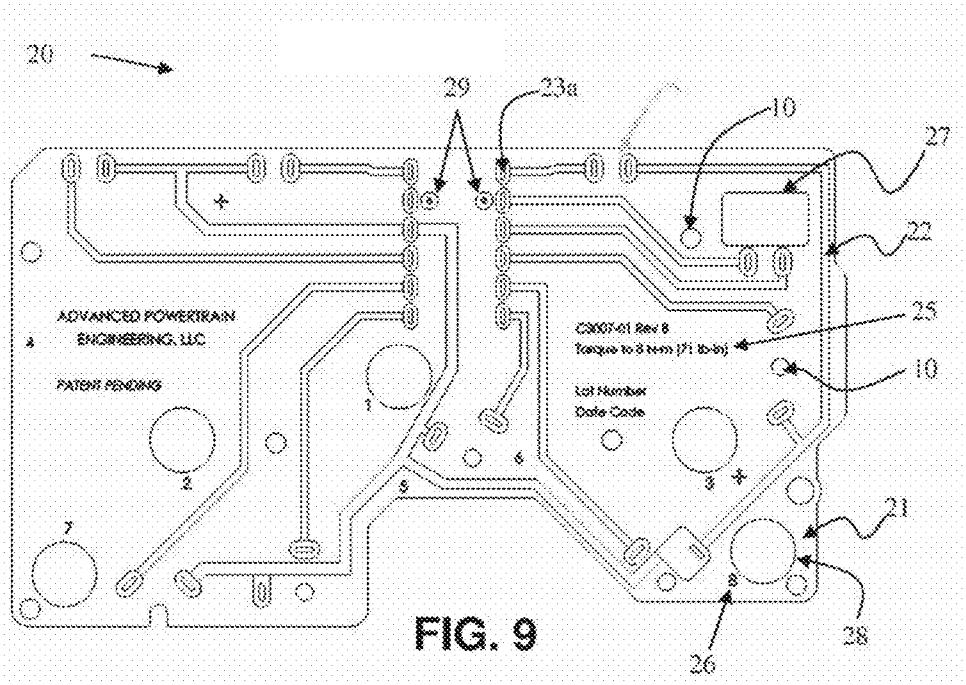
FIG. 9 shows the front side of one embodiment of the invention.
Figure 10:
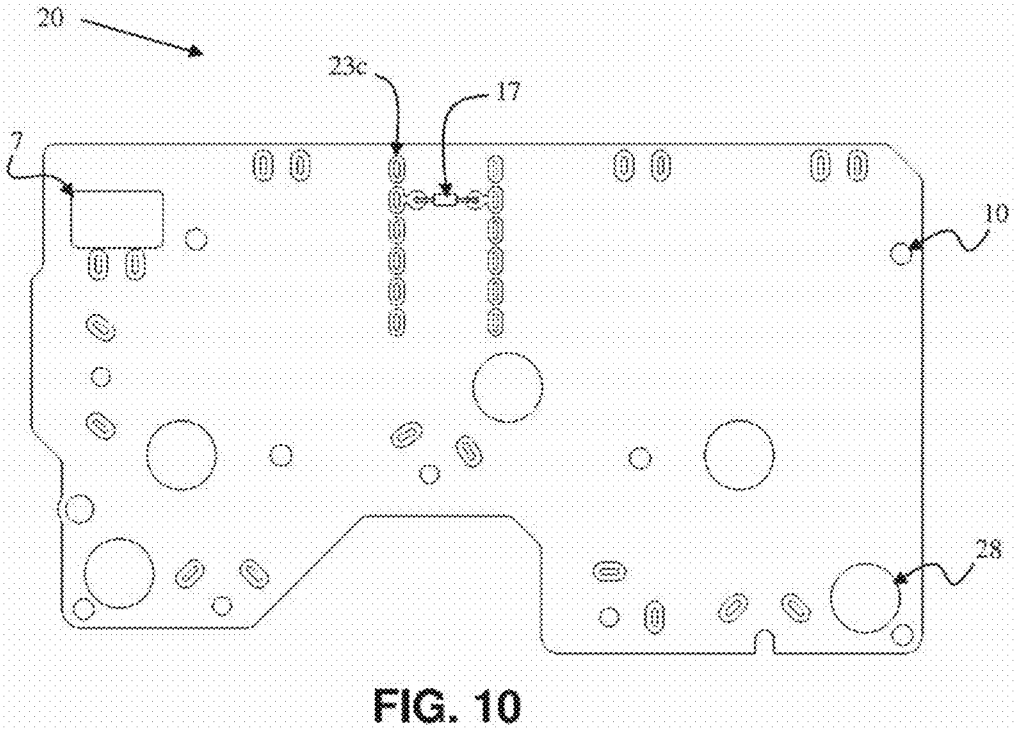
FIG. 10 shows the back side of the apparatus of FIG. 9.
Figure 11A:
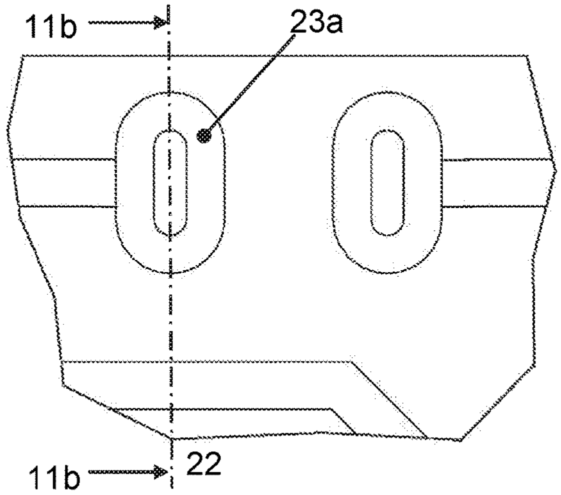
FIG. 11*a* is a depiction a front side view of an interconnect area according to one embodiment of the present invention.
Figure 11B:
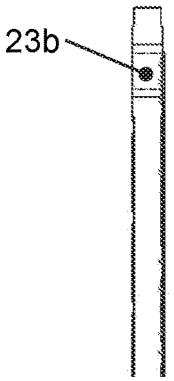
FIG. 11*b* is a cross-sectional view of an interconnect area opening according to one embodiment of the present invention.
Figure 11C:
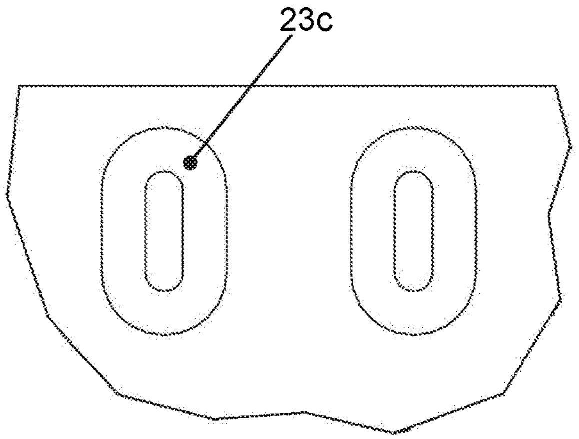
FIG. 11*c* is a view of the apparatus of FIG. 11*a* from the rear.
Figure 12:
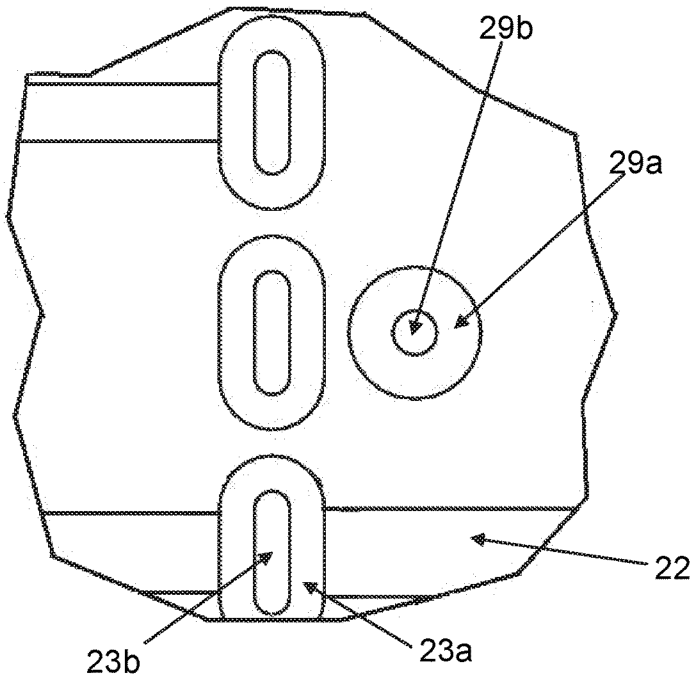
FIG. 12 is a depiction of a backside view of an interconnect area according to one embodiment of the present invention.
Figure 13:
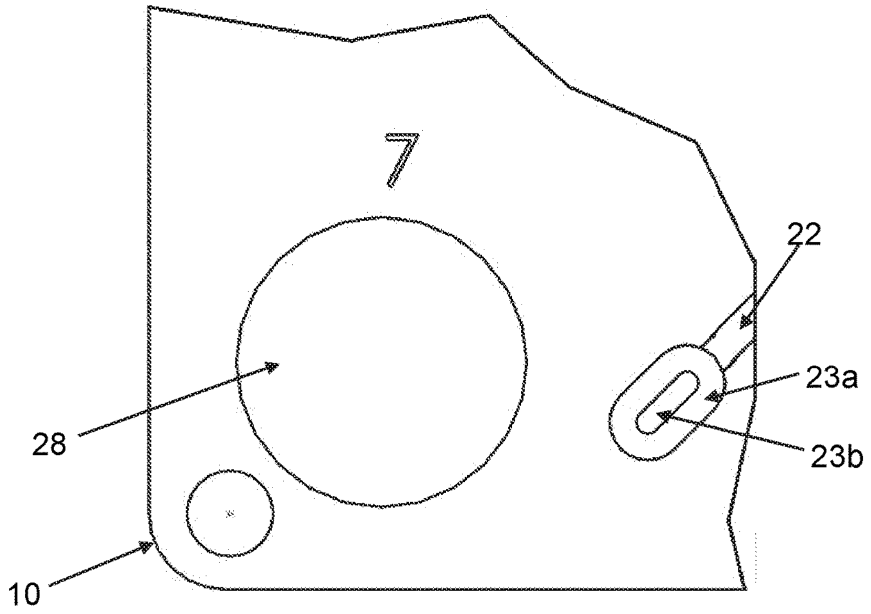
FIG. 13 is a depiction of a typical bolt clearance according to one embodiment of the present invention.

A thermistor (17) is inserted across the two pins denoted (29) in FIG. 9. The thermistor preferably has a resistance of about 30 k ohm at 25° C. and is soldered into place. However, the thermistor may be crimped into place as well. After insertion and connection of the thermistor with the PCB, the unit is herein referred to as a PCA.

After insertion of the PCA on the module and the subsequent soldering of the terminal pins, a cover may be inserted over the PCA to protect the assembly during installation into the vehicle. The preferred material of the cover is a thermoplastic such as Nylon 6/6 with 30% glass filler. One or more mechanical fasteners may also be used to provide mechanical connection of the PCA to the module assembly. This would relieve the soldered connections from physically supporting the PCA and help alleviate possible vibration.

Figure 14:
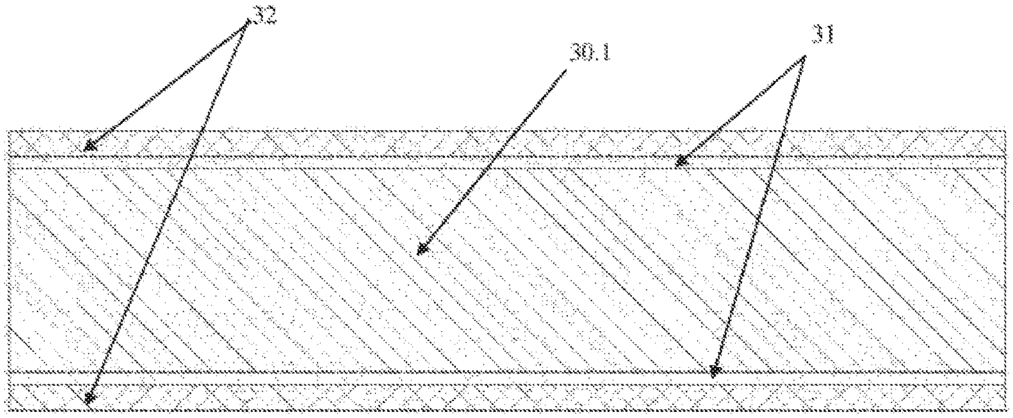
FIG. 14 is a cross-sectional view of a PCA according to one embodiment of the present invention.
Figure 15:
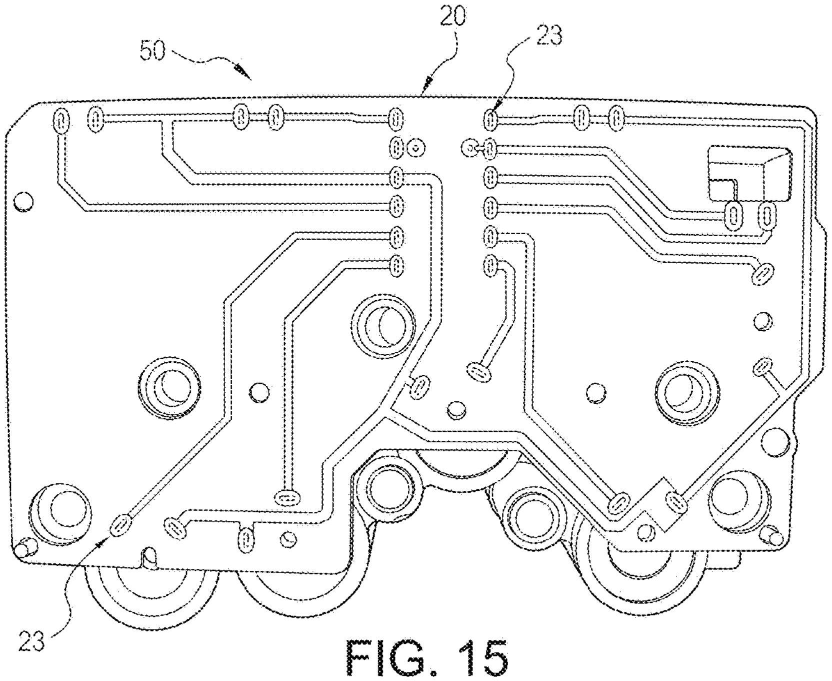
FIG. 15 is a photographic representation of the PCA assembled on the solenoid module according to one embodiment of the present invention.
Figure 16:
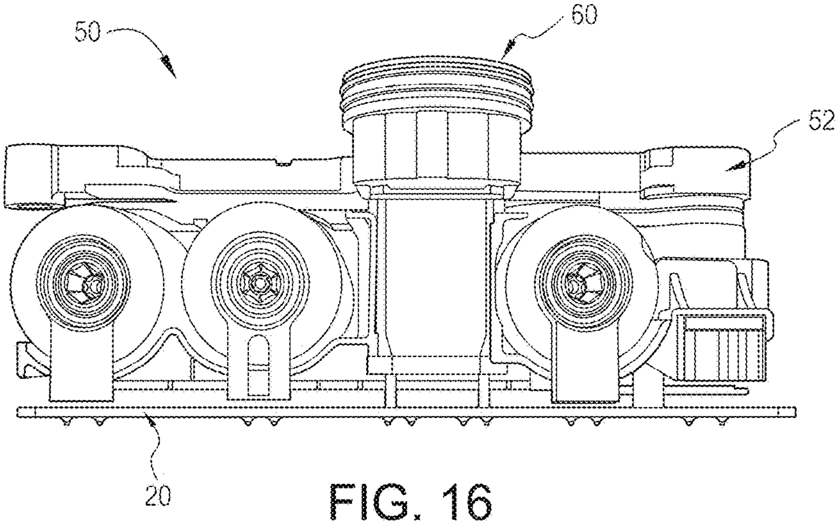
FIG. 16 shows a side view of the apparatus of FIG. 15.
Figure 17:
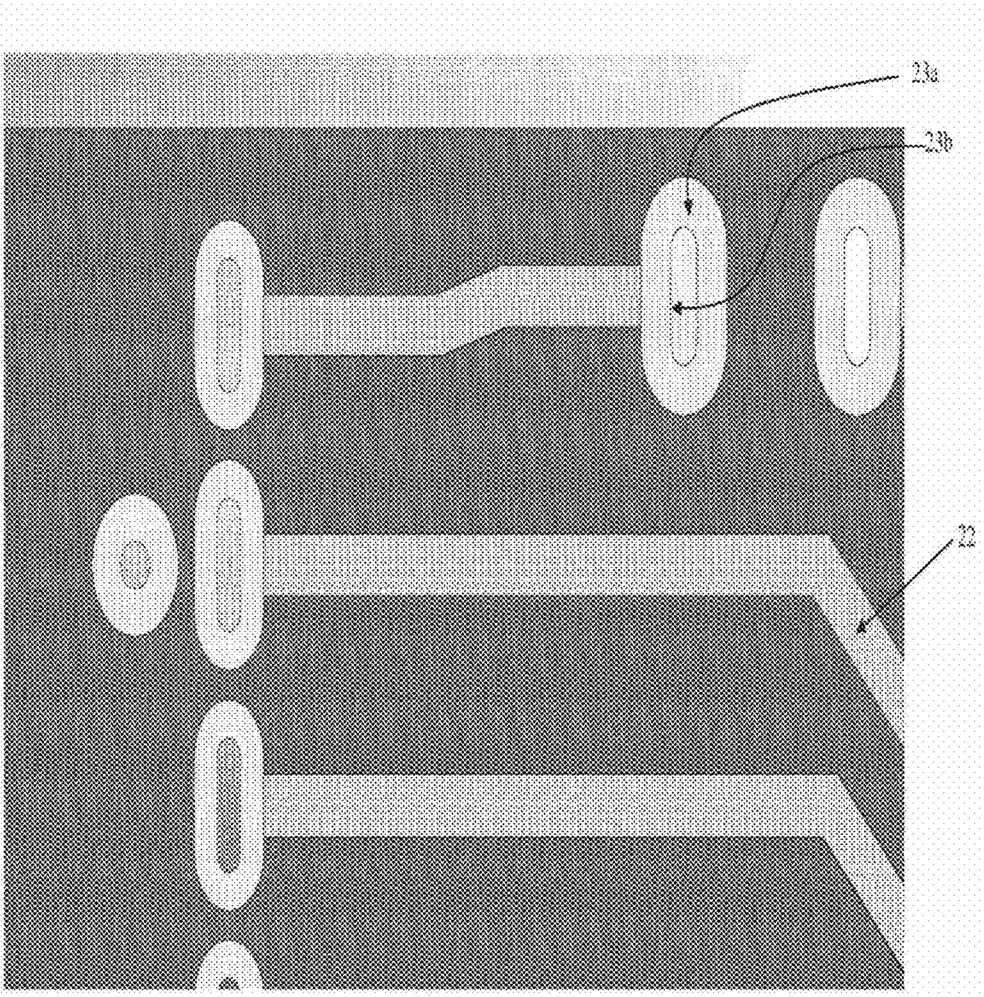
FIG. 17—Front side enlarged view of a PCA according to one embodiment of the present invention.
Figure 18:
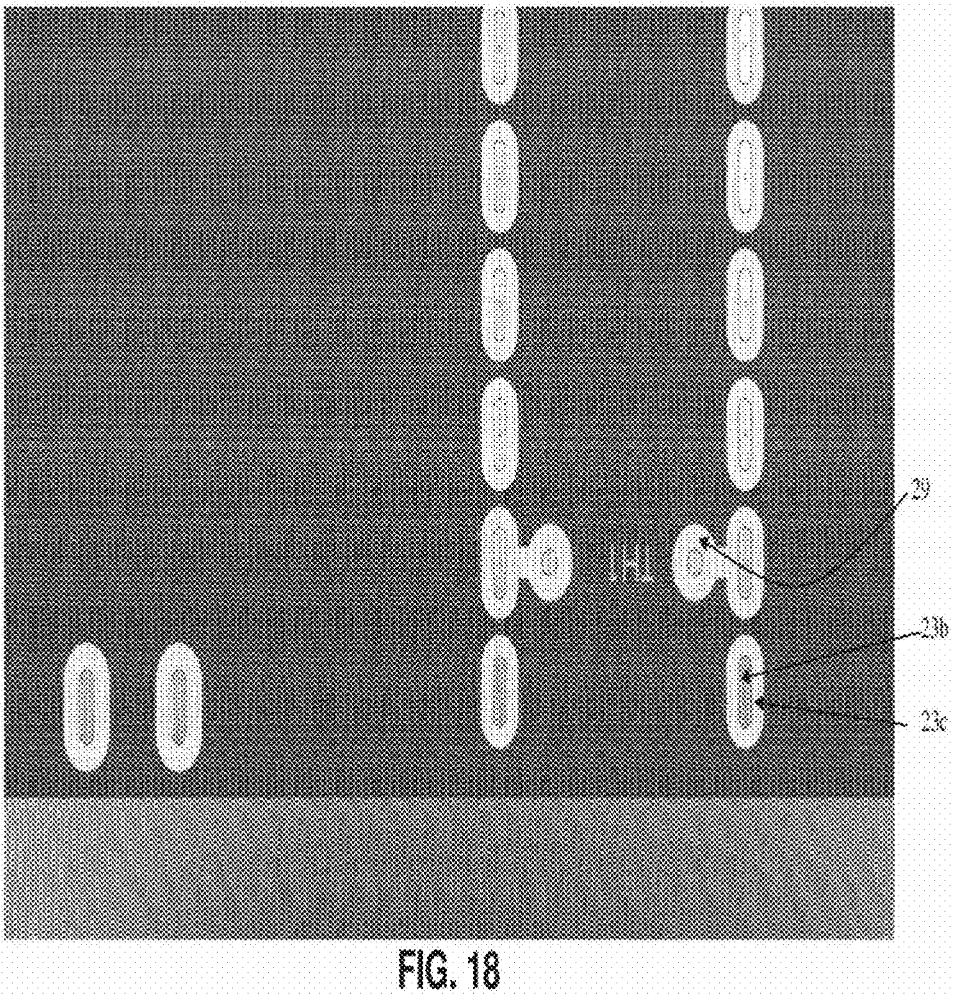
FIG. 18—Back side enlarged view of the apparatus of FIG. 17.
Figure 19:
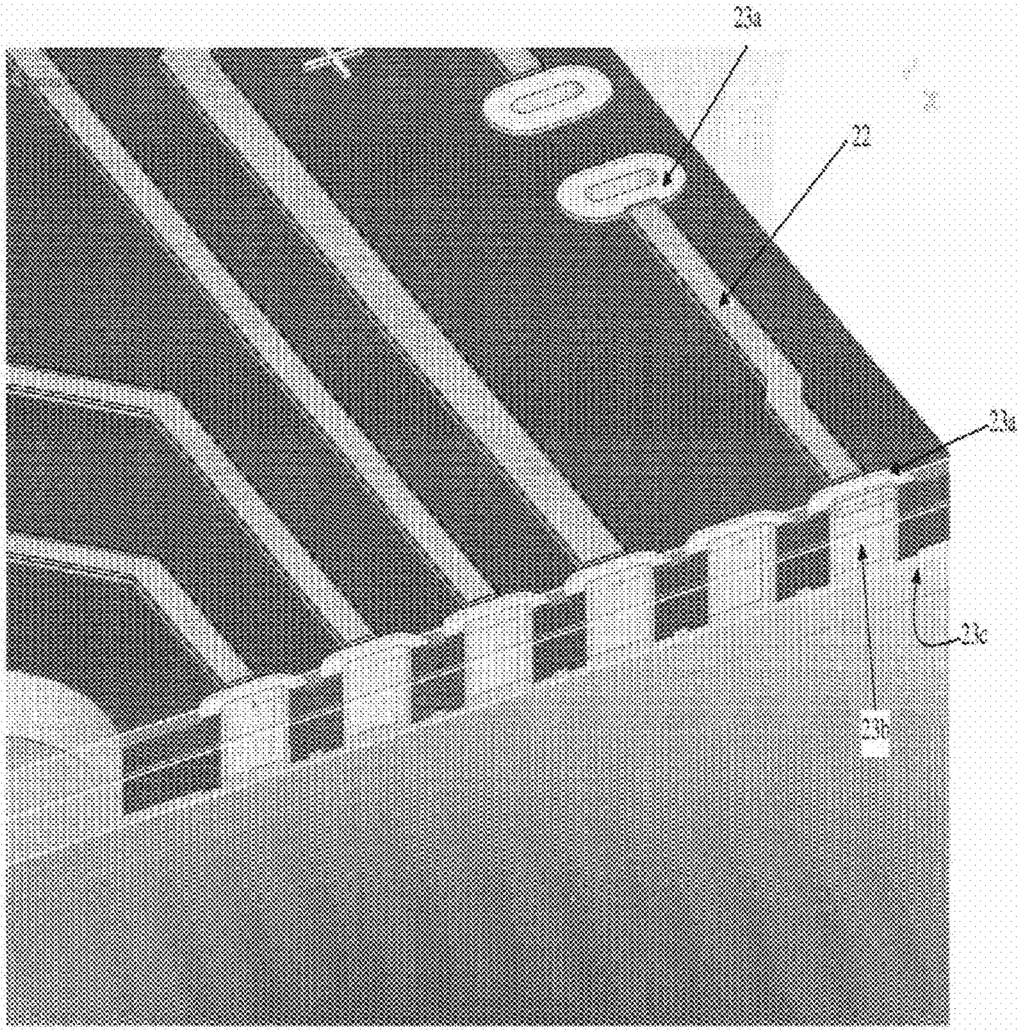
FIG. 19—Cross sectional enlarged view of the apparatus of FIG. 17 showing conductive walls of interconnection holes.

Referring to FIG. 14, which includes a cross sectional view of a typical circuit trace (22), the printed circuit board (PCB) core (30.1) is comprised of Flame Retardant 4 (FR-4) epoxy resin material. The core is cut to form the geometry shown in FIGS. 9 and 10, including bolt clearance holes (28), interconnect holes (23), thermistor holes (29), connector window hole (27) and miscellaneous module feature clearance holes (10). Six pairs of interconnect areas (23) can be seen in the general center of the PCA assembly (20). Interconnect areas (23) each include a front side interconnect pad (23*a*) comprising conductive material and in electrical communication with a circuit trace 22; a hole (23*b*) with electrically conductive surfaces; and an electrically conductive interconnect area (23*c*) on the backside of PCA (20). Six pairs of interconnect holes (23) provide electrical communication to the terminal housing (60). PCA (20) includes a plurality of other interconnect areas (23) throughout the area of the PCA.

The PCB is plated with copper (31) on the front side to form the circuit traces (22), interconnect areas (23), and printed text areas (25) (26). The PCB is plated with copper (31) on the back side to form the interconnect areas (23). A green solder mask (32) is applied on both sides in all areas except in the interconnect areas (23). A solder layer is applied over exposed copper in the interconnect areas (23) to aid with solder connection to module solenoids and connector terminals. This layer forms an exposed front pad (23*a*), back pad (23*c*) and the walls of the through hole (23*b*). Final overall thickness of the PCB is approximately 1.6 mm.

In the preferred embodiment of the invention, a thermistor (17) is inserted from the backside in the thermistor holes (29) and soldered in place, thermistor holes (29) include an electrically conductive area (29*a*) on the front side of PCB 20; a through hole (29*b*) having electrically conductive inner surfaces; and an interconnect area (29*c*) on the backside of PCB 20. The preferred thermistor is a negative temperature coefficient (NTC) type that has a nominal resistance of 30 k ohms at 25° C. with a beta coefficient (K) of approximately 3900.

Figure 7:
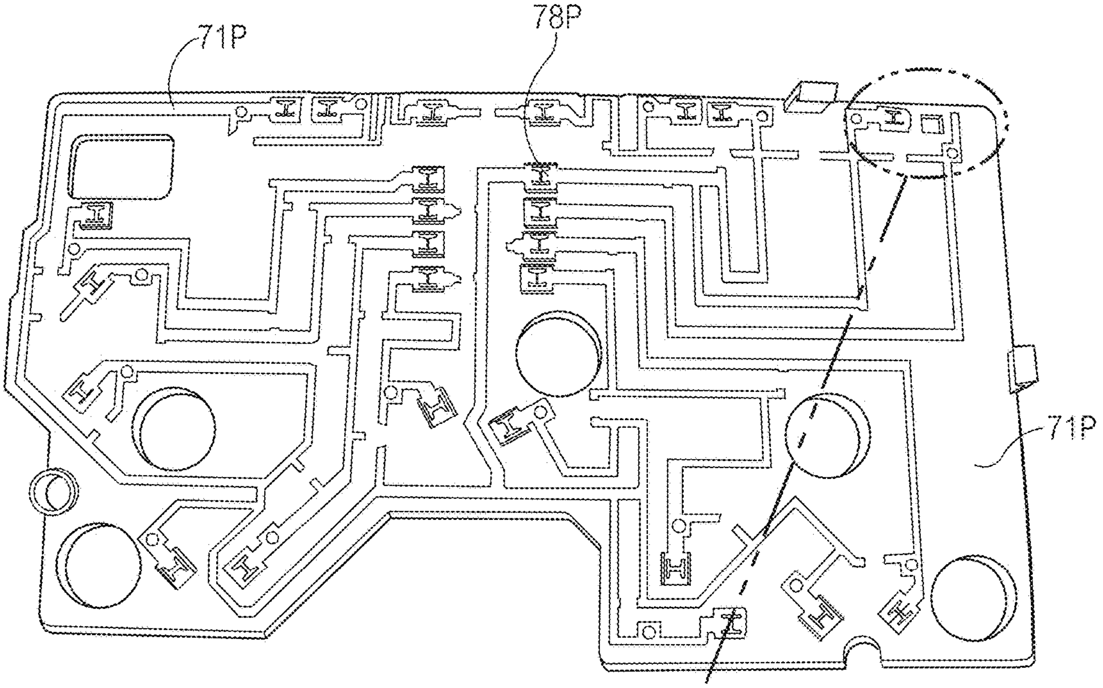
FIG. 7: Typical failure mode of a known CBA design.
Figure 7A:
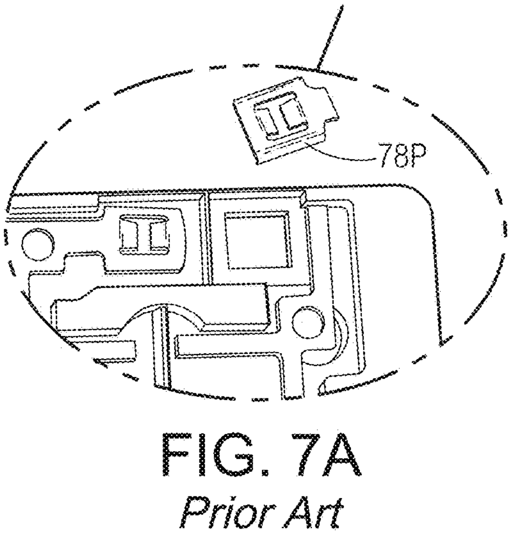
FIG. 7A is a partial view of the design depicted in FIG. 7

Upon assembly of the thermistor with the PCB, the printed circuit assembly (PCA) is assembled onto the rebuilt solenoid module (50) and soldered in place. A complete functional testing of the assembly is performed. There are several aspects to the use of various embodiments of the present invention with electro-hydromechanical assemblies, such as the 5R55S, 5R55W and 5R55N solenoid modules. First, the connection between the circuitry and the solenoids and connection terminals are more robust than the original barbed style connectors and better able to withstand vibration and mechanical loading. Second, the masked circuit traces printed on the PCA are less susceptible to contamination. Third, the circuit traces are not susceptible to the mechanical stress that cause the original circuit tracks to break, as shown in FIG. 7. Fourth, the preferred embodiment provides instructions to the end user that aids installation. For example, the specified bolt torque of 8 N-m is communicated by text (25). Also, the specified torque sequence is communicated by text (26). This eliminates the need for the end user to research the specifications or to install without the required information. It also helps to prevent returned assemblies because of improper installation.

While the inventions have been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An apparatus for an automatic transmission, comprising:

a plurality of solenoid valves, each said valve having a pair of electrical terminals for receiving electrical power, each terminal having straight parallel walls, the parallel walls having a first length, each terminal being adapted and configured for frictional connection to an electrical circuit;

a printed circuit board having a plurality of through holes each adapted and configured for a soldered connection, each said through hole having straight parallel walls separated by a width, the end of each parallel wall being interconnected to the end of the facing parallel wall by a curved surface, each said hole defining a second length separating the curved surfaces at the ends, the second length being greater than the first length, and wherein each said terminal is inserted in a different one of each said through holes and soldered to the parallel walls of the respective said through hole.

2. The apparatus of claim 1 wherein each terminal has a width between parallel walls, at least one curved surface is semi-cylindrical having a diameter, and the diameter of the semi-cylinder is about equal to or greater than the width.

3. The apparatus of claim 2 wherein the diameter of the semi-cylinder is greater than the width.

4. The apparatus of claim 1 wherein the printed circuit board is planar and having a thickness, each said through hole extends through the thickness, the parallel walls of each said through hole are coated with an electrically conductive material, and each said terminal and said through hole are soldered at least along the first length.

5. The apparatus of claim 1 wherein the printed circuit board has a thickness, each said through hole extends through the thickness, the parallel walls and the curved surfaces of each said through hole are coated with an electrically conductive material, and each said terminal and the straight parallel walls of corresponding through hole are soldered together.

6. The apparatus of claim 1 wherein the automatic transmission has an internal volume wetted with fluid, wherein said plurality of solenoids and said printed circuit board are located within the internal volume.

7. The apparatus of claim 1 wherein said printed circuit board includes a generally planar board, said board incorporating the plurality of through holes, said board having a surface including printed indicia for installing said apparatus in the automatic transmission.

8. The apparatus of claim 1 wherein said printed circuit board includes a generally planar board having front and rear faces, said board incorporating the plurality of through holes, said board having conductive material deposited around each said through hole on both front and rear surfaces and conductive material deposited on the surfaces of said through hole.

9. The apparatus of claim 1 which further includes a thermistor.

10. The apparatus of claim 2 wherein each terminal is adapted and configured for spring-loaded frictional connection to an electrical circuit.

11. The apparatus of claim 2 wherein each terminal is adapted and configured for frictional connection to a barbed electrical circuit.

12. The apparatus of claim 2 wherein each terminal is adapted and configured for frictional connection to an electrical circuit by way of a press-fit.

13. The apparatus of claim 5 wherein each terminal is adapted and configured for frictional connection to an electrical circuit by way of a press-fit.

14. A method for repairing a solenoid module of an automatic transmission, comprising:

providing a used solenoid module that includes a plurality of solenoid valves each having a terminal electrically interconnected to a source of electrical power by at least one spring-loaded frictional fit;

disconnecting each terminal from the source at the respective frictional fit;

providing a printed circuit board having a plurality of through holes, each through hole including at least one straight internal surface;

soldering each disconnected terminal to a different one of the through holes; and attaching the soldered printed circuit assembly to the solenoid module.

15. The method of claim 14 wherein the frictional fits are integrated into a used circuit assembly, and which further comprises discarding the used circuit assembly.

16. The method of claim 14 wherein the frictional fits are barbed connections.

17. The method of claim 14 wherein the through holes have two straight, parallel sides, and the terminal has a rectangular cross-sectional shape.

18. The method of claim 14 wherein said providing includes a used automatic transmission for a road vehicle, and which further comprises placing the soldered printed circuit board within the used transmission.

19. The method of claim 14 wherein said attaching is before said soldering.

20. The method of claim 14 wherein said providing includes an existing circuit board assembly having conductive tracks enclosed in an insulator, and said disconnecting is from the existing circuit board assembly.

* * * * *